United States Patent
Cheung et al.

(10) Patent No.: US 9,999,617 B2
(45) Date of Patent: Jun. 19, 2018

(54) COMPOSITIONS FOR TREATING BACTERIAL INFECTIONS

(75) Inventors: Ambrose Cheung, Hanover, NH (US); Zhibiao Fu, King of Prussia, PA (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 1409 days.

(21) Appl. No.: 13/379,784

(22) PCT Filed: Jul. 1, 2010

(86) PCT No.: PCT/US2010/040696
§ 371 (c)(1),
(2), (4) Date: Jan. 25, 2012

(87) PCT Pub. No.: WO2011/002951
PCT Pub. Date: Jan. 6, 2011

(65) Prior Publication Data
US 2012/0122877 A1    May 17, 2012

Related U.S. Application Data

(60) Provisional application No. 61/222,305, filed on Jul. 1, 2009.

(51) Int. Cl.
*A61K 31/425*    (2006.01)
(52) U.S. Cl.
CPC .................................. *A61K 31/425* (2013.01)
(58) Field of Classification Search
CPC .................................................. A61K 31/426
USPC ....................................................... 514/369
See application file for complete search history.

(56) References Cited

U.S. PATENT DOCUMENTS 5,208,250 A * 5/1993 Cetenko et al. ............... 514/369

FOREIGN PATENT DOCUMENTS

WO    WO 02062337 A1 *  8/2002

OTHER PUBLICATIONS

Buts et al. "Toxin-Antitoxin Modules as Bacterial Metabolic Stress Managers" Trends in Biochemical Sciences 2005 vol. 30(12):672-679.
Christensen et al. "Toxin-antitoxin Loci as Stress-response-elements: ChpAK/MazF and ChpBK Cleave Translated RNAs and are Counteracted by tmRNA" Journal of Molecular Biology 2003 vol. 332:809-819.
Condon, C. "Shutdown Decay of mRNA" Molecular Microbiology 2006 vol. 61(3):573-583.
Donegan, N.P. and Cheung, A.L. "Regulation of the *mazEF* Toxin-Antitoxin Module in *Staphylococcus aureus* and Its Impact on *sigB* Expression" Journal of Bacteriology 2009 vol. 191(8):2795-2805.
Fu et al. "Characterization of MazF$_{Sa}$, an Endoribonuclease from *Staphylococcus aureus*" Journal of Bacteriology 2007 vol. 189(24):8871-8879.
Fu et al. "Overexpression of MazF$_{Sa}$ in *Staphylococcus aureus* Induces Bacteriostasis by Selectively Targeting mRNAs for Cleavage" Journal of Bacteriology 2009 vol. 191(7):2051-2059.
Gerdes et al. "Prokaryotic Toxin-Antitoxin Stress Response Loci" Nature Reviews Microbiology 2005 vol. 3:371-382.
Kamada et al. "Crystal Structure of the MazE/MazF Complex: Molecular Bases of Antidote-Toxin Recognition" Molecular Cell 2003 vol. 11:875-884.
Kamphuis et al. "Structure and Function of Bacterial Kid-Kis and Related Toxin-Antitoxin Systems" Protein & Peptide Letters 2007 vol. 14:113-124.
Zhang et al. "MazF Cleaves Cellular mRNAs Specifically at ACA to Block Protein. Synthesis in *Escherichia coli*" Molecular Cell 2003 vol. 12:913-923.

* cited by examiner

*Primary Examiner* — Shengjun Wang
(74) *Attorney, Agent, or Firm* — Licata & Tyrrell P.C.

(57) ABSTRACT

The present invention is antibiotic compositions having the ability to disrupt a MazEF complex in *S. aureus*. The compositions also have the ability to inhibit growth of *S. aureus* and as such are useful as antibiotic compounds.

2 Claims, No Drawings

COMPOSITIONS FOR TREATING BACTERIAL INFECTIONS

INTRODUCTION

This application is a U.S. National Stage Application of PCT/US2010/040696 filed Jul. 1, 2010 and claims benefit of priority to U.S. Provisional Application Ser. No. 61/222,305, filed Jul. 1, 2009, the contents of each of which are incorporated herein by reference in their entirety.

BACKGROUND OF THE INVENTION

Toxin and antitoxin (TA) systems are commonly found in prokaryotes. These systems function to allow the organisms to rapidly adjust rates of protein and DNA synthesis in order to respond to external stimuli and/or stress (Gerdes et al. 2005. *Nature Rev. Microbiol.* 3:371-382). Under normal circumstances, TA genes are co-transcribed and co-translated as part of an operon so that both antitoxin and toxin are produced together within the cytosol to form an inert complex. Under specific stress, transcription of the TA promoter will be repressed, disrupting transcription and subsequently translation. As toxins are stable compounds while the antitoxins compounds are more labile and prone to proteolytic attack by bacterial Lon/ClpP proteases, disruption of transcription from the TA promoter results in excess toxin and activity of the toxin in the cell. The target of such toxins may be mRNA, DNA gyrase or DNA helicase, where interaction of toxin with these targets leads to disruption of transcription and translation of genes responsible for important cellular processes.

Based on sequence homology and cellular targets, there are eight major TA systems that have been identified in prokaryotes (Gerdes et al. 2005. *Nature Rev. Microbiol.* 3:371-382; Kamphius et al. 2007. *Protein Peptide Lett.* 14:113-124). Among these TA systems is the MazEF system, which includes the toxin MazF and the antitoxin MazE. These two proteins form a linear heterohexamer made up of alternating toxin and antitoxin homodimers (Kamada et al. 2003. *Mol. Cell.* 11:875-884). The MazEF TA complex in *E. coli* has been shown to autoregulate by binding of the DNA by the N-terminal domain of MazE. The MazF toxin has been shown to cleave translated mRNAs and through this mechanism to block protein synthesis within prokaryotic cells (Christensen et al. 2003. *J. Mol. Biol.* 332:809-819). The cleavage of mRNAs in *E. coli* is at ACA sites (Zhang et al. 2003. *Mol. Cell.* 12:913-923). A variety of conditions have been shown to trigger the activity of MazF in prokaryotic cells including for example, stress linked to high temperatures, oxidative stress, DNA damage by thymidine starvation, UV irradiation, and contact with protein-inhibiting antibiotics (Kamphius et al. 2007. *Protein Peptide Lett.* 14:113-124). Although MazEF clearly functions as a bacteriostatic system (Gerdes et al. 2005. *Nature Rev. Micrabiol.* 3:371-382) within prokaryotic cells, it is not clear whether MazEF also functions within cells as a system for programmed cell death.

Sequence analysis has revealed that the MazF toxin is more conserved among different bacteria than is the antitoxin MazE. This finding is consistent with the finding that the activity of similar TA systems in different bacteria is dependent on the specificity of the antitoxin. In fact, it has been found that *Staphylococcus aureus* MazEF homologs are quite different from *E. coli* MazEF homologs (Fu et al. 2007. *J. Bacteriol.* 189:8871-8879; Fu et al. 2009. *J. Bacteriol.* 191:2051-2059; Niles et al. 2009. *J. Bacteriol.* 191: 2795-2805). It has been found through transcriptional analysis that the mRNA target of the toxin MazF in *S. aureus* is selective, sparing important transcripts such as gyrA and recA (Niles et al. 2009. *J. Bacteriol.* 191:2795-2805). Therefore, in *S. aureus* MazF has features of a bacteriostatic effect rather than a bacteriocidal effect. The effect can be reversed by MazE, but only within a specific time window beyond which the cells would become nonviable.

Based on the importance of TA systems within cells, including the MazEF system, interest has grown in the use of these systems in the development of new antibiotic compounds. To date, the only organisms not identified as having MazEF systems are *Mycobacerium leprae, Chlymidia, Rickettsia*, and *Mycoplasm*. MazEF has been found to be an important TA system within a variety of prokaryotes including *E. coli, S. aureus*, and *S. pneumonia*. There remains a need for new antibiotic compounds active against clinically important bacteria.

SUMMARY OF THE INVENTION

The present invention features a pharmaceutical composition composed of a compound that disrupts *Staphylococcus aureus* MazE-MazF antitoxin-toxin complex, said compound being in admixture with a pharmaceutically acceptable vehicle. In one embodiment, the compound inhibits the growth of *S. aureus*. In another embodiment, the compound has the structure of Formula (I):

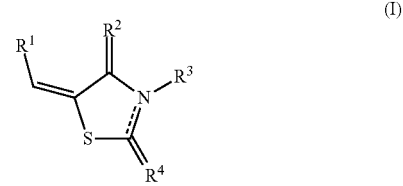

wherein $R^1$ is a substituted or unsubstituted aryl group, $R^2$ is O or S, or $R^1$ and $R^2$ together form a substituted or unsubstituted aryl; $R^3$ is absent, H, alkyl or substituted or unsubstituted aryl group; $R^4$ is O, S, an amide or sulfonamide; and wherein the dashed bond is present or absent. In certain embodiments, the compound is Compound 1, Compound 2, Compound 6, Compound 7, Compound 8, Compound 14, Compound 16, or a derivative or analog thereof. In other embodiments, the compound is a compound listed in Table 1 or Table 2. Methods for inhibiting the growth of *S. aureus* and preventing or treating an *S. aureus* infection with an effective amount of the composition of the invention are also provided.

DETAILED DESCRIPTION OF THE INVENTION

The present invention is a series of antibiotic compounds that have activity to disrupt the MazEF complex in *S. aureus* and to inhibit growth of *S. aureus* in vitro. The compounds were identified by screening a 50,000 compound library from ChemBridge (DIVERSet). Ten compounds were identified with the ability to disrupt the MazEF complex in *S. aureus* and to inhibit growth of the bacteria. The screening assay used to identify the compounds is based on detection of fluorescence that results when the candidate compound cleaves a hybrid RNA-DNA MazF substrate.

The screening assay is based on an understanding of the cleavage site on mRNA that is attacked by MazF in *S. aureus*. The cleavage site of the MazF toxin of *S. aureus* on mRNA was identified to be VUUV' where V and V' are adenine (A), cytosine (C) or guanine (G), but not uracil (U). A hybrid RNA-DNA hybrid molecule was developed. The hybrid molecule that was synthesized contained 12 bases. The hybrid contained the 4-base recognition site (AUUC) of MazF from *S. aureus*, and flanked the 4-bases on each side with 4 DNA bases. On one end of the hybrid molecule the fluorescence marker FAM-6 was attached while at the other end the quencher BHG-1 was attached. The resulting RNA-DNA hybrid molecule does not yield significant fluorescence unless the RNA target site is cleaved by the MazF toxin to separate FAM-6 from BHG-1. This hybrid molecule has been used as the substrate for an antibiotic screening assay and was used to identify the antibiotic compounds of the instant invention.

In order to identify compounds as antibiotic compounds with potential activity against *S. aureus*, experiments were performed wherein MazEF complex of *S. aureus* was incubated with the hybrid molecule substrate and the compounds, which were to be tested for activity to disrupt the MazEF complex. Compounds that disrupted the complex cleaved the hybrid fluorescence substrate and yielded detectable fluorescence. The results of this screening assay identified the compounds listed in Table 1.

TABLE 1

| Compound # | Compound Structure and Name | ChemBridge ID # | MIC (μg/ml) |
|---|---|---|---|
| 1 | 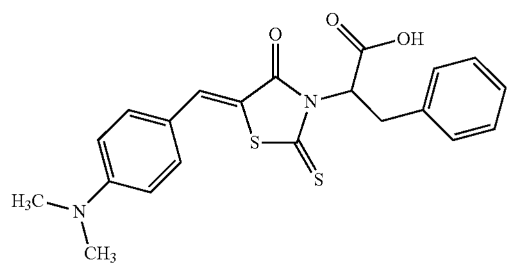  2-{5-[4-(dimethylamino)benzylidene]-4-oxo-2-thioxo-1,3-thiazolidin-3-yl}-3-phenylpropanoic acid | 6048022 | 12.5 |
| 2 | 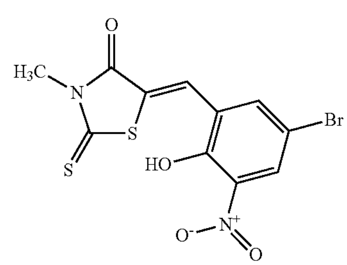  5-(5-bromo-2-hydroxy-3-nitrobenzylidene)-3-methyl-2-thioxo-1,3-thiazolidin-4-one | 5902920 | 12.5 |
| 3 | 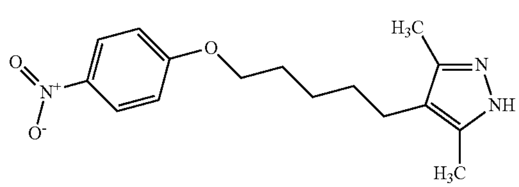  3,5-dimethyl-4-[5-(4-nitrophenoxy)pentyl]-1H-pyrazole | 5362508 | ND |

TABLE 1-continued
| Compound # | Compound Structure and Name | ChemBridge ID # | MIC (µg/ml) |
|---|---|---|---|
| 4 | 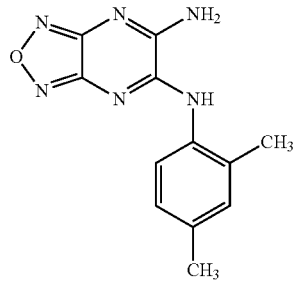<br>N-(2,4-dimethylphenyl)[1,2,5]oxadiazolo[3,4-b]pyrazine-5,6-diamine | 5380590 | 12.5 |
| 5 | 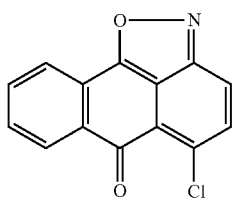<br>5-chloro-6H-anthra[1,9-cd]isoxazol-6-one | 5468117 | 6.25 |
| 6 | 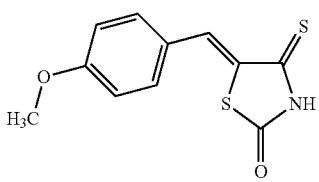<br>5-(4-methoxybenzylidene)-4-thioxo-1,3-thiazolidin-2-one | 5761926 | 0.78 |
| 7 | 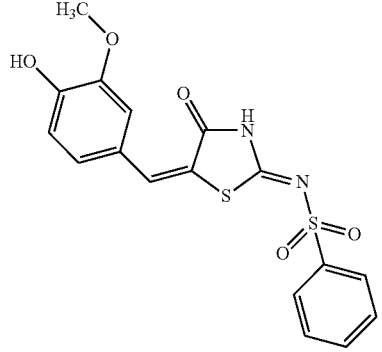<br>N-[5-(4-hydroxy-3-methoxybenzylidene)-4-oxo-1,3-thiazolidin-2-ylidene]benzenesulfonamide | 5957303 | 100 |

TABLE 1-continued

| Compound # | Compound Structure and Name | ChemBridge ID # | MIC (μg/ml) |
|---|---|---|---|
| 8 | 3,4-dimethoxy-N-(6-methyl-1,3-benzothiazol-2-yl)benzamide | 5564414 | ND |
| 9 | 2-({[(4-chlorophenyl)amino]carbonyl}amino)-6-ethyl-4,5,6,7-tetrahydrothieno[2,3-c]pyridine-3-carboxamide | 6131237 | 100 |
| 10 | | 5215283 | 100 |

Once the compounds of the present invention were identified through the MazEF screening assay described above, the activity of the compounds to inhibit growth of *S. aureus* in vitro was tested using the standard method of determining Minimum Inhibitory Concentrations (MICs). Such methods are well known to those of skill in the art since determining MIC doses is a standard assay in development of antibiotic drugs. For example, MIC values can be determined according to the Clinical and Laboratory Standards Institute guidelines. In Table 1, the MIC values are presented for each of the ten compounds identified through the MazEF screening assay as having potential for antibiotic activity in *S. aureus*.

In addition to the above screen, an additional screen was employed. In this second assay, compounds from a compound library (natural or synthetic compounds) were incubated with either wild-type bacteria (with the MazEF complex) or a mazEF mutant of *S. aureus*. When the compound of interest disrupts the MazEF complex of *S. aureus* to free up the toxin (MazF), the mRNA-cleavage toxicity of the toxin is available to kill the parental strain; however, the isogenic mazEF mutant will not be killed. Using this assay, the compounds listed in Table 2 were identified as inhibiting the growth of wild-type strain Newman but not the isogenic mazEF mutants.

TABLE 2

| Compound # | Structure | ChemBridge ID # |
|---|---|---|
| 11 |  N-(2-hydroxy-4-nitrophenyl)-2,2-bis(4-methylphenyl)cyclopropanecarboxamide | 5634518 |

TABLE 2-continued

| Compound # | Structure | ChemBridge ID # |
|---|---|---|
| 12 | 4-(1-acetyl-2-oxopropyl)-3-chloro-1,2-naphthalenedione | 5286499 |
| 13 | 2,2-dichloro-N-(4-nitrophenyl)-3-phenylcyclopropanecarboxamide | 6079510 |
| 14 | 5-(3-iodo-4-methoxybenzylidene)-2-thioxo-1,3-thiazolidin-4-one | 5486272 |
| 15 | 2,4-dichloro-5-(5-nitro-2-furyl)benzoic acid | 6047950 |
| 16 | 5-benzylidene-4-thioxo-1,3-thiazolidin-2-one | 5765232 |

The compounds disclosed herein can be used as is, or used as lead compounds which are further refined and optimized using synthetic medicinal chemical methods in order to enhance their activity against S. aureus. Such compounds are typically structurally related analogs or derivatives of the compounds listed in Tables 1 and/or 2, which retain the ability to disrupt the S. aureus MazE-MazF antitoxin-toxin complex. For example, the compounds disclosed herein can be modified to include additional substituents (e.g., O, N, S, OH, CH$_3$, halo groups, phenyl groups, alkyl groups, etc.), remove substituents (e.g., O, N, S, OH, CH$_3$, halo groups, phenyl groups, alkyl groups, etc.), or substitute groups (e.g., substitute one halo group for another) in order to provide analogs with improved activity and/or efficacy. As with the initial screens, modified compounds or compound analogs or derivatives can be screened using the assays described herein.

In particular embodiments, the invention embraces a compound of Formula (I):

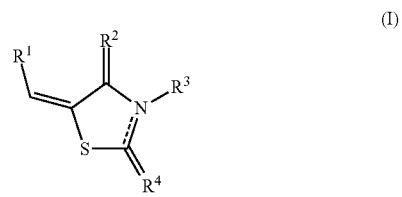

(I)

wherein $R^1$ is a substituted or unsubstituted aryl group; $R^2$ is O or S; or $R^1$ and $R^2$ together form an aryl group, which may be substituted or unsubstituted. Furthermore, in other embodiments, the dashed bond may be present or absent, $R^3$ can be absent, H, alkyl or an unsubstituted or substituted aryl (e.g., phenylpropanoic acid); and $R^4$ is O, S, an amide (e.g., dimethyoxybenzamide) or sulfonamide (e.g., benezenesulfonamide).

For the purposes of the present invention, an aryl, as a group or substituent per se, refers to an aromatic carbocyclic radical containing 6 to 14 carbon atoms, preferably 6 to 10 carbon atoms, unless indicated otherwise. Suitable aryl groups include phenyl, napthyl and biphenyl. Substituted aryl groups include the above-described aryl groups which are substituted one or more times by halogen (e.g., Br, I, F, or Cl), alkyl, hydroxy, alkoxyl (e.g., methoxy), nitro, methylenedioxy, ethylenedioxy, amino, nitryl, alkylamino, dialkylamino (e.g., dimethlyamino), hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy) groups.

An alkyl group is defined as a straight-chain or branched-chain aliphatic hydrocarbon radical having preferably 1 to 5 carbon atoms ($C_{1-5}$), especially 1 to 4 carbon atoms ($C_{1-4}$) or most desirably 1 to 3 carbon atoms ($C_{1-3}$). Suitable alkyl groups include methyl, ethyl, propyl, isopropyl, butyl, sec-butyl, tert-butyl, and pentyl.

Alkoxyl means alkyl-O— groups in which the alkyl portion preferably has 1 to 6 carbon atoms, especially 1 to 4 carbon atoms, or desirably 1 to 2 carbon atoms. Suitable alkoxyl groups include methoxy, ethoxy, propoxy, isopropoxy, isobutoxy, sec-butoxy, pentoxy, hexoxy, heptoxy, and octoxy. Preferred alkoxyl groups are methoxy and ethoxy.

Compounds of Formula (I) particularly embraced by the present invention include Compounds 1, 2, 6, 7, 8, 14, and 16, and derivatives or analogs thereof. By way of illustration, representative analogs of Compounds 1, 2, 7, 8, and 14 include, but are not limited to, the compounds listed in Table 3.

TABLE 3

| Compound # | Analog Structure and Name | ChemBridge ID # |
|---|---|---|
| 1 | 2-(5-benzylidene-4-oxo-2-thioxo-1,3-thiazolidin-3-yl)-3-phenylpropanoic acid | 5856304 |
|  | 2-[5-(4-methylbenzylidene)-4-oxo-2-thioxo-1,3-thiazolidin-3-yl]-3-phenylpropanoic acid | 5559681 |
|  | 2-[5-(4-hydroxybenzylidene)-4-oxo-2-thioxo-1,3-thiazolidin-3-yl]-3-phenylpropanoic acid | 5527255 |
|  | 2-[5-(4-nitrobenzylidene)-4-oxo-2-thioxo-1,3-thiazolidin-3-yl]-3-phenylpropanoic acid | 5859999 |
|  | 2-[5-(4-chlorobenzylidene)-4-oxo-2-thioxo-1,3-thiazolidin-3-yl]-3-phenylpropanoic acid | 5856439 |
| 2 | 5-(3-bromo-2-hydroxy-5-nitrobenzylidene)-3-methyl-2-thioxo-1,3-thiazolidin-4-one | 5604641 |
|  | 5-(5-bromo-2-hydroxy-3-nitrobenzylidene)-3-ethyl-2-thioxo-1,3-thiazolidin-4-one | 5672432 |
|  | 5-(3-bromo-2-hydroxy-5-nitrobenzylidene)-3-ethyl-2-thioxo-1,3-thiazolidin-4-one | 5669233 |
|  | 5-(2-hydroxy-3-nitrobenzylidene)-3-methyl-2-thioxo-1,3-thiazolidin-4-one | 5615884 |
|  | 5-(2-hydroxy-5-nitrobenzylidene)-3-methyl-2-thioxo-1,3-thiazolidin-4-one | 5482997 |
| 7 | N-[5-(3,4-dimethoxybenzylidene)-4-oxo-1,3-thiazolidin-2-ylidene]benzenesulfonamide | 5848186 |
|  | N-[5-(3,4-dimethoxybenzylidene)-4-oxo-1,3-thiazolidin-2-ylidene]-4-methylbenzenesulfonamide | 5526442 |
|  | N-[5-(3,4-dimethoxybenzylidene)-3-methyl-4-oxo-1,3-thiazolidin-2-ylidene]-4-methylbenzenesulfonamide | 5727406 |
|  | N-[5-(4-hydroxybenzylidene)-4-oxo-1,3-thiazolidin-2-ylidene]benzenesulfonamide | 5966662 |
| 8 | 3-methoxy-N-(6-methyl-1,3-benzothiazol-2-yl)benzamide | 5525483 |
|  | N-(4,6-dimethyl-1,3-benzothiazol-2-yl)-3,4-dimethoxybenzamide | 7936315 |
|  | N-1,3-benzothiazol-2-yl-3,4-dimethoxybenzamide | 5274582 |
| 14 | 5-(4-hydroxy-3-iodobenzylidene)-2-thioxo-1,3-thiazolidin-4-one | 5713557 |
|  | 5-(3-iodobenzylidene)-2-thioxo-1,3-thiazolidin-4-one | 5376606 |
|  | 5-(4-methoxybenzylidene)-3-methyl-2-thioxo-1,3-thiazolidin-4-one | 5483392 |
|  | 3-ethyl-5-(4-hydroxy-3-iodobenzylidene)-2-thioxo-1,3-thiazolidin-4-one | 7096079 |

Compounds of the present invention are prepared using routine chemical procedures known to those skilled in the art. Likewise, the compounds can be purified to homogeneity using conventional approaches and verified using routine NMR analysis.

Compounds listed in Table 1 and/or Table 2, or their derivatives or analogs, can be further tested in vivo to validate efficacy in the prevention or treatment of S. aureus infection. There are many different in vivo model systems that can be used by one of skill in the art to further demonstrate efficacy and aid in identification of doses that will be both safe and effective in humans. Such animal model systems are well-accepted and used during development of new human pharmaceuticals that will undergo scrutiny by various regulatory bodies worldwide and approved for use in humans. Examples of such model systems include but are not limited to a guinea pig model of S. aureus wound infection (Kernodle, D. S, and A. B. Kaiser. 1994. Antimicrob. Agents Chemother. 38:1325-1330); a rabbit model of S. aureus abscess in rabbits (Fernandez et al. 1999. Antimicrob. Agent Chemother. 43:667-671); a mouse model of S. aureus skin infection (Gisby, J. and J. Bryant. 2000. Antimicrob. Agents Chemother. 44:255-260); a mouse model of deep dermal S. aureus infection (Godin et al. 2005. J. Antimicrob. Chemother. 55:989-994); and a mouse intraperitoneal infection model (Patel et al. 2004. Antimicrob. Agents Chemother. 48:4754-4761). In such models, drugs can be tested against infections where the infection established is from inoculation of the animal with various strains of S. aureus. Demonstration of efficacy in such models is measured in many ways and would include but not be limited to a reduction in mortality rate, a reduction in bacterial cell counts determined by microscopic examination of tissue or blood samples taken from the animals, or even assessment of wound healing in the animals.

The efficacy of a drug that has been screened in vitro and shown to have activity to inhibit growth of S. aureus including methicillin-susceptible S. aureus (MSSA), methicillin-resistant S. aureus, (MRSA) and community-acquired methicillin-resistant S. aureus (CA-MRSA) can be further examined using the model described by Patel et al. (2004. Antimicrob. Agents Chemother. 48:4754-4761). Briefly, Swiss mice (6 mice per dose group, 4 weeks of age) will be inoculated intraperitoneally (i.p.) with 0.5 ml of bacterial suspension so that each mouse will receive from $2 \times 10^8$ to $3 \times 10^8$ CFU of isolate. The drug to be tested, or the combination of drugs to be tested, is then at a dose shown to be effective in vitro but also known to be safe in animals. The doses to be tested are routinely chosen by those of skill in the art by using clinical judgment based on results of in vitro pharmacological assays. For example, doses can be ones that are equivalent to an $ED_{10}$, an $ED_{25}$, an $ED_{50}$, and an $ED_{75}$ for inhibiting bacterial growth in vitro. The drug will be administered at 1 and 4 hours after i.p. inoculation of mice with isolates. The drug to be tested can be administered subcutaneously, intravenously, or orally. A vehicle control group will be used. All mice are observed for survival up to 7 days. Efficacy of the test drug will be measured as an increased survival rate as compared to control animals (untreated) and as compared to survival in a group of animals administered a positive control agent (e.g., an antibiotic known to have efficacy to treat S. aureus).

A mouse model of S. aureus skin infection (e.g. Godin et al. 2005. J. Antimicrob. Chemother. 55:989-994) will be used to examine the efficacy of a drug that has been screened in vitro and shown to have activity to inhibit growth of isolates. Briefly, 4 to 5 week old immunocompetent ICR male mice will be used. Three groups of mice each will be inoculated intracutaneously with isolates. The intracutaneous injections will be applied to the back of each animal that will have been previously shaved with clippers. Six mice from each group will be inoculated with 0.1 ml of saline containing $10^7$, $10^8$ or $10^9$ CFU/ml of isolate. The mice are then examined daily for development of deep dermal abscesses, inflammatory reaction in the inoculated area and wound size for a total of 3 weeks. The drug to be tested for antibiotic activity can be given orally, by intravenous injection or dermally. If dermal administration is to be tested, the drug will be spread over the area of the abscess. The dose of test drug to be administered will be chosen based on the results of in vitro studies of inhibition of bacterial growth. As discussed above, doses can be chosen based on the percentage of growth inhibition seen in vitro. The test drug will be administered 72 hours after intracutaneous injection with MSSA, MRSA and CA-MRSA inoculates and can last for 7 days or longer depending on the response of the animals to the treatment. At the end of 7 days treatment, animals will be sacrificed and the skin area corresponding to the infection site and underlying tissues can be processed for bacterial count and histopathological examination. Alternatively, mice can be sacrificed at various times, at least 3 mice per time period, such as 1, 3, and 7 days in order to monitor the progression of infection in response to the test drug.

It is contemplated that one of skill in the art will choose the most appropriate in vivo model system depending on the type of drug product being developed. Some in vivo models are more amenable to oral or intravenous injection while others are more desirable for dermal application methods. The medical literature provides detailed disclosure on the advantages and uses of a wide variety of such models.

Once a test drug, or a combination of drugs, has shown to be effective in vivo in animals against MSSA, MRSA, and CA-MRSA, and that the emergence of resistance upon exposure to the compound is low, clinical studies can be designed based on the doses shown to be safe and effective in animals. One of skill in the art will design such clinical studies using standard protocols as described in textbooks such as Spilker (2000. *Guide to Clinical Trials*. Lippincott Williams & Wilkins: Philadelphia).

Having demonstrated that the compounds herein can inhibit the growth of *S. aureus*, the present invention features use of one or more of these compounds, or their derivatives or analogs, in the preparation of a pharmaceutical composition or medicament for use in inhibiting the growth of *S. aureus* and in the prevention or treatment of a *S. aureus* infection. Pharmaceutical compositions of the invention can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

As the data here indicate, compounds of the present invention inhibit the growth of *S. aureus*. Accordingly, the compounds of the present invention find use in methods of preventing or treating an *S. aureus* infection. According to such methods, a subject in need of treatment (e.g., a subject with or at risk of developing an *S. aureus* infection) is administered an effective amount of a composition of the invention so that the *S. aureus* infection is prevented or treated. Subjects benefiting from this treatment include those exhibiting clinical signs or symptoms of an *S. aureus* infection or subject exposed to *S. aureus* or suspected of being exposed to *S. aureus*. Effective treatment will result in a decrease, attenuation, inhibition or amelioration of the well-known signs or symptoms of an *S. aureus* infection.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

What is claimed is:

1. A topical pharmaceutical composition consisting of a compound that disrupts *Staphylococcus aureus* MazE-MazF antitoxin-toxin complex, said compound being in admixture with a pharmaceutically acceptable vehicle, wherein the compound is

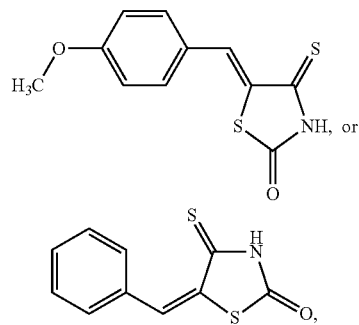

and wherein the pharmaceutically acceptable vehicle comprises an emulsifier for topical application of the composition.

2. The composition of claim 1, wherein the compound inhibits the growth of *S. aureus*.

* * * * *